United States Patent [19]

Nelson

[11] Patent Number: 4,947,468
[45] Date of Patent: Aug. 7, 1990

[54] BYPASS TANDEM CHAMBER CHARGE DENSITY MONITOR

[75] Inventor: J. Keith Nelson, Schenectady, N.Y.

[73] Assignee: Electric Power Research Institute, Inc., Palo Alto, Calif.

[21] Appl. No.: 325,932

[22] Filed: Mar. 20, 1989

[51] Int. Cl.$^5$ .................... G01N 27/60; G01R 29/12; H05F 1/00

[52] U.S. Cl. ................................ 324/453; 324/454; 324/464

[58] Field of Search ...................... 73/861.09; 137/551; 324/453, 72, 71.1, 452, 454, 464

[56] References Cited

U.S. PATENT DOCUMENTS

| | | | |
|---|---|---|---|
| 3,405,722 | 10/1968 | Carruthers | 324/453 |
| 4,041,375 | 8/1977 | Polukhina | 324/454 |
| 4,249,131 | 2/1981 | Owen | 324/452 |
| 4,309,661 | 1/1982 | Kamoto | 324/454 |
| 4,392,110 | 7/1983 | Elmenshawy | 324/453 |
| 4,592,240 | 6/1986 | McHale | 324/453 |

FOREIGN PATENT DOCUMENTS 0650024  5/1979  U.S.S.R. ............................ 324/453

Primary Examiner—Gerard R. Strecker
Assistant Examiner—Jose M. Solis
Attorney, Agent, or Firm—Leonard Bloom

[57] ABSTRACT

A bypass conduit is connected to a primary conduit and has tandem reservoirs formed therein. Continuous measurements are taken from the respective reservoirs of the electrical current generated by the relaxing fluid therein and flowing to ground. These respective measurements are inputted to a microcomputer through respective electrometer elements and converted into a single measure of charge density along with readings of the moisture, conductivity and temperature of the fluid. In a preferred embodiment, the fluid constitutes the oil (or other coolant) circulated in respective conduits between a power transformer and an external heat exchanger. The microcomputer may trigger an alarm (or a control mechanism) whenever the charge density generated in the circulating coolant reaches a predetermined threshold level, thereby avoiding a potential hazardous condition due to the build-up of static electrical charges in the protected transformer or other device.

25 Claims, 6 Drawing Sheets

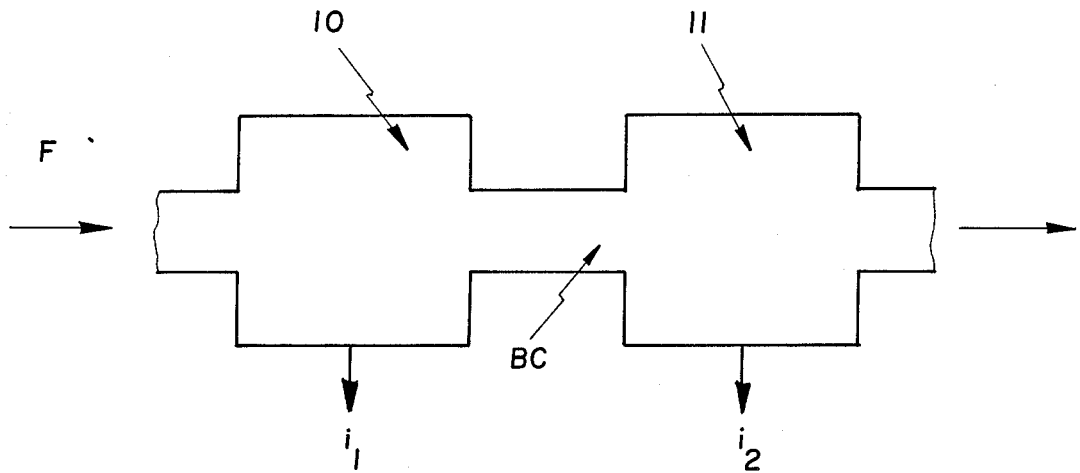

FROM THEVENIN .... $i_1/i_2 = \exp\left[-t/T\right]$

SINCE $i_1 = P_o Q \left[1 - \exp(-t/T)\right]$

THEN: $P_o Q = \dfrac{i_1}{1 - i_2/i_1}$ $Q = \dfrac{i_1}{P\left[1 - \dfrac{i_2}{i_1}\right]}$

WHERE $i_1$ = ELECTRICAL CURRENT FLOWING FROM FIRST FLUID RESERVOIR TO GROUND (AMPERES)

$i_2$ = ELECTRICAL CURRENT FLOWING FROM SECOND FLUID RESERVOIR TO GROUND (AMPERES)

P = FLOW RATE OF FLUID THROUGH THE BYPASS SYSTEM (CUBIC METERS/SECOND)

Q = CHARGE DENSITY OF FLUID t = RESIDENCE TIME OF THE FLUID

T = RELAXATION TIME OF THE FLUID

FIG. 3

BYPASS TANDEM CHAMBER CHARGE DENSITY MONITOR

FIELD OF THE INVENTION

The present invention relates to an apparatus and method for measuring fluid charge density, and more particularly, to an apparatus and method for measuring the electrostatic charge buildup in oil or other coolants circulating through electrical power systems and equipment such as power transformers and the like.

BACKGROUND OF THE INVENTION

As a fluid flows through a conduit or other restriction, static electrical charges are generated. If the fluid itself is not highly conductive, the charges do not leak away; but rather, there is a progressive build-up leading to significant charge densities. Because of the electrostatic field associated with these charges (either in the bulk or on surfaces) there may be a significant risk of fire or explosion if a spark should occur, especially if the fluid itself is combustible. Over the years, advanced designs have led to faster flow rates in fluid transfer systems and, as a result, the problems associated with electrostatic buildup have become more severe.

The dangers of electrostatic charge build-up during the pumping of hydrocarbon fuels are well-known, and the aviation industry has chosen to control such unwanted charge by the use of additives in the fuels. However, this solution is not practical for insulating fluids which are circulated in power system equipment, such as in power transformers The recent incidence of failure of large power transformers has generated the need for a simple, robust and reliable means to measure the charge density present in the oil circulating in a power transformer due to the streaming electrification process inherent in the pumping of the fluid, so that an alarm or corrective action may be initiated.

Another solution to this problem involved the monitoring of the electrostatic buildup until an upper level threshold was reached, at which point the charges could be dissipated using a charge neutralizer.

For example, an early method suspended a metallic sphere in the liquid. As the fluid passed by the sphere, the charged particles accumulated on the sphere; and a voltmeter measured the sphere's electrical potential. However, this method failed to give an accurate measurement because the fluid colliding with the sphere itself generated an excess charge which resulted in a false measurement.

If the fluid was pumped through an electrically isolated chamber, the relaxation of the charge in that chamber could be measured in terms of the current to ground. However, this cannot be interpreted as the charge density in the fluid unless the relaxation is completed, that is, the residence time in the chamber has to be large in comparison with the relaxation time of the fluid (which is largely determined by its conductivity). In some circumstances, this simple method may be used by providing suitable electrical isolation for the external transformer radiators (or other heat exchangers) so that they may be used as a relaxation chamber. However, this simple method has a disadvantage in that errors will accrue if relaxation in the chamber is not complete.

In U.S. Pat. No. 3,405,722 issued to Carruthers et al, a method was disclosed for making a more accurate charge density measurement by bleeding a small amount of fluid away from the primary conduit and into a bypass conduit having a fluid reservoir therein, and the electrostatic charge density of the fluid was measured by means of an electric field meter while the fluid remained in the reservoir. Thereafter, the fluid was returned to the primary conduit. However, this Carruthers et al '722 patent involved the use of a parallel diminutive simulation tank to mimic the behavior of the larger tank to be monitored, and the use of non-identical fluid paths involved inherent errors. A "scale factor" had to be empirically determined for the method to work, and there was no guarantee that this scale factor would be a constant, that is, independent of fluid properties, ambient conditions and flow regime. In particular, this scale factor was a function of fluid conductivity. Additionally, this system did not yield accurate measurements because electric field meters are inherently subject to interference.

U.S. Pat. No. 3,306,320 issued to Bond disclosed the use of an electrometer to measure the electrostatic phenomena in a branch line. However, this Bond '320 patent used the static electricity generating propensity of a fluid to detect changes in the fluid composition, and not for measuring the charge carried by the fluid itself. Moreover, this system required a means to periodically withdraw the fluid, rather than taking a continuous indication of charge; and the principle inherent in the Bond '320 patent involved the generation of a fluid charge and not the monitoring of the relaxation of the fluid.

In U.S. Pat. No. 4,309,661 issued to Kamoto, an electrically conductive segment of a bypass conduit absorbed the electrical charges carried by the fluid as the fluid traveled through the bypass conduit, and the charges were transferred to ground. An ammeter interrupted the ground path to provide a measurement of the electrical current generated by the charged fluid. A flow-rate measurement was also taken of the fluid in the bypass conduit, and the fluid charge density was calculated from current and flow rate using a well-known equation. However, to achieve an accurate measurement, the segment of electrically conductive bypass conduit had to be of sufficient length to permit the absorption of almost all of the electric charges in the electrified fluid. Meeting this constraint was a serious disadvantage and limitation, and contributed a source of error, especially in applications involving very high flow rates. Additionally, the bypass loop had a very small pressure drop between the entrance and exit ports to drive the flow, and the disclosure in Kamoto '661 did not employ a ram jet effect. Moreover, the entry region in Kamoto '661 was unscreened, and the charge migration to the walls contributed to errors in view of the low speed of bypass flow required to prevent charge segregation.

The following additional background patents are further illustrative of the prior art:

| Inventor(s) | U.S. Pat. No. |
| --- | --- |
| Polukhina et al | 4,041,375 |
| Owen | 4,249,131 |
| El-Menshawy et al | 4,392,110 |
| McHale et al | 4,592,240. |

SUMMARY OF THE INVENTION

Accordingly, it is an object of the present invention to alleviate the disadvantages and deficiencies of the prior art by providing a means for accurately and continuously measuring the charge carried by a fluid, wherein the measurement is entirely independent of the fluid relaxation time (that is, the fluid conductivity) as well as the residence time of the fluid.

It is another object of the present invention to provide at least two substantially-identical isolated reservoirs (or chambers) in the fluid flow path, to measure currents (using electrometer type elements) in both chambers, and to calculate the charge density using an arithmetic conversion equation.

It is yet another object of the present invention to provide a bypass conduit having first and second reservoirs formed therein, the reservoirs being laterally spaced with respect to each other and in series communication therewith, together with a means for taking first and second measurements of the electrical relaxation current associated with the fluid in the bypass conduit and flowing to ground in the respective reservoirs, and a means for arithmetically converting the first and second measurements into a single measure which is independent of both the conductivity of the fluid, as well as the residence time of the fluid in the first and second reservoirs (or chambers) in the bypass conduit.

It is yet still another object of the present invention to provide a grounded metallic screen for the bypass conduit.

It is a further object of the present invention to provide an apparatus and method which is especially suited for use in measuring the charge density of oil circulating in power systems equipment, such as in power transformers.

It is a still further object of the present invention to provide an apparatus and method for the sampling of fluid from discrete points within a fluid transfer system by use of a pump for the induction of fluid into a bypass conduit, where an accurate charge density measurement can be made.

It is a yet still further object of the present invention to measure the charge density in the circulating fluid in the bypass conduit independent of the conductivity of the fluid and, alternately, for measuring the conductivity of the fluid using the same components of the programmed computerized system, albeit in a different operating mode.

In accordance with the teachings of the present invention, there is herein illustrated and described, an improved apparatus for measuring the quantity of static electric charges carried by a fluid flowing through a primary conduit means, wherein a bypass conduit means is provided in a substantially parallel configuration with the primary conduit means (for intercepting the flow of fluid therein) and is electrically insulated therefrom. A portion of the fluid is temporarily diverted from the primary conduit means into the bypass conduit means, and the charge density of the fluid in the bypass conduit means is continually measured while the fluid is flowing therein at a rate which is less than the rate of the fluid flowing in the primary conduit means. In this combination, a first reservoir means and a second reservoir means are formed in the bypass conduit means. The second reservoir means is laterally spaced from the first reservoir means and is in series communication therewith. Means are provided for taking a first measurement of the electrical relaxation current associated with the fluid in the first reservoir means and flowing to ground, and means are provided for taking a second measurement of the electrical relaxation current associated with the fluid in the second reservoir means and flowing to ground. Means are further provided for arithmetically converting the first and second measurements into a single measure representative of the charge in the fluid, such that the single measure is independent of both the conductivity of the fluid, as well as the residence time of the fluid in the first and second reservoirs.

In a preferred embodiment, the first and second reservoirs are substantially identical.

Preferably, the last-named means for arithmetically converting the first and second measurements utilizes the equation:

$$Q = \frac{i_1}{P[1 - i_2/i_1]}$$

wherein
Q=the charge density of the fluid in the bypass conduit means (Coulombs/cubic meter);
$i_1$=the electrical current generated by the fluid in the first reservoir means and flowing to ground (amperes);
$i_2$=the electrical current generated by the fluid in the second reservoir means and flowing to ground (amperes); and
P=the flow rate of fluid in the bypass conduit means (cubic meters/second).

In a preferred embodiment, the means for arithmetically converting further comprises a microcomputer means. The microcomputer means measures additional fluid properties (including temperature, moisture, conductivity and imposed AC stress) and the microcomputer means conditions the measurement of fluid charge density through the use of parameter performance envelopes based on the measurements of additional fluid properties.

In a different embodiment, the measurement and derivation of a charge density may be accomplished by battery-powered analog electronics, thus rendering the instrument completely self-contained with no moving parts.

Viewed in another aspect, the present invention constitutes an improved method for measuring the quantity of static electrical charges carried by a fluid flowing through a primary conduit means, wherein a bypass conduit means is provided in a substantially parallel configuration with the primary conduit means (for intercepting the flow of fluid therein) and electrically insulated therefrom, wherein a portion of the fluid is temporarily diverted from the primary conduit means into the bypass conduit means, and wherein the charge density of the fluid in the bypass conduit means is continually measured while the fluid is flowing therein at a rate which is less than the rate of the fluid flowing in the primary conduit means. The improved method includes the steps of providing a first reservoir means in the bypass conduit means; and further providing a second reservoir means in the bypass conduit means, laterally spaced from the first reservoir means, and in series communication therewith. A first measurement is taken of the electrical relaxation current associated with the fluid in the first reservoir means and flowing to ground, and a second measurement is taken of the electrical relaxation current associated with the fluid in the second reservoir means and flowing to ground. The first and second measurements are arithmetically converted into a single measure representative of the charge in the fluid, such that this single measure is independent of both the conductivity of the fluid and of the residence time of the fluid in the first and second reservoirs. Preferably, the arithmetic conversion of the first and second measurements takes place in a microprocessor or microcomputer.

The teachings of the present invention find particular utility in a power transformer having a coolant (such as oil) circulated therein, wherein the coolant is pumped into a heat exchanger through a suitable conduit. The microcomputer, in turn, may trigger an alarm (or a cut-off mechanism) whenever the conditioned fluid charge density of the coolant exceeds a predetermined threshold value, thereby avoiding a potentially hazardous condition.

These and other objects of the present invention will become apparent from a reading of the following specification, taken in conjunction with the enclosed drawings.

BRIEF DESCRIPTION OF THE DRAWINGS

FIG. 3 is a schematic diagram and chart, showing how the first and second measurements are arithmetically converted using the Thevenin equation.

GENERAL DESCRIPTION OF THE PREFERRED EMBODIMENTS

Figure 1:
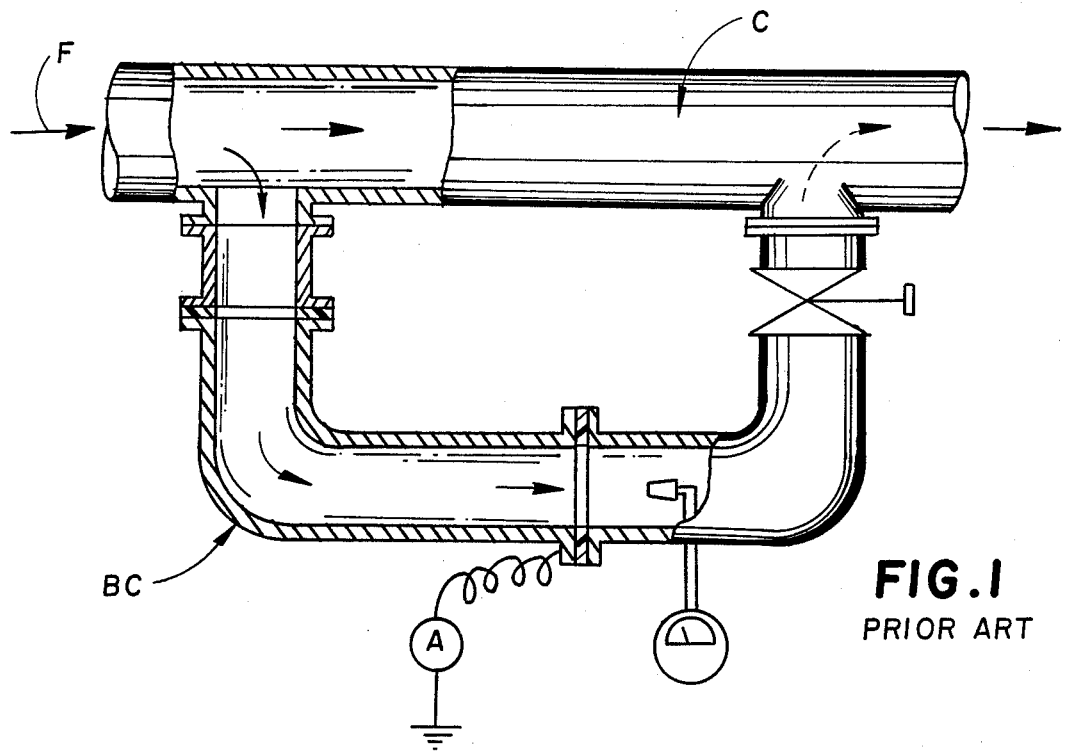
FIG. 1 is a schematic illustration of a prior art method for measuring the fluid charge density in a bypass conduit (such as disclosed in the aforesaid Kamoto '661 patent).

With reference to FIG. 1, there is illustrated a prior art method for measuring the fluid charge density in a bypass conduit BC connected to a conduit C through which a fluid F is flowing. The electrical current flowing from the bypass conduit BC to ground is measured in an electrometer A. As previously noted, this prior art method is inherently disadvantageous, since the bypass conduit BC must be sufficiently long to absorb almost all of the electrical charges in the electrified fluid, thereby constituting a serious limitation and source of error.

Figure 2:
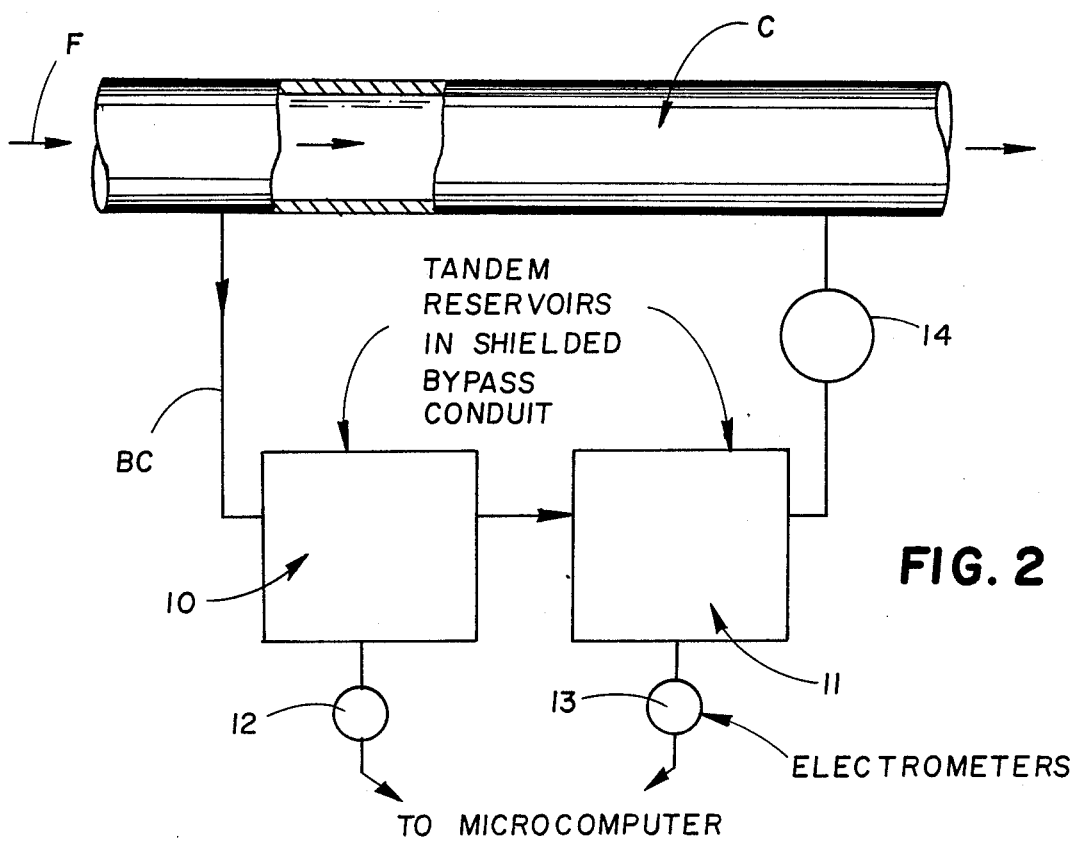
FIG. 2 is a schematic illustration of the present invention, showing the improvement wherein first and second measurements are taken in tandem in respective chambers or reservoirs which are formed in the bypass conduit, laterally spaced and in series communication with each other.

With reference to FIG. 2, and as distinguished from the prior art, the present invention provides a first fluid chamber or reservoir 10 and a second fluid chamber or reservoir 11 in the bypass conduit BC, which is fully electrically screened by suitable means (not shown). These first and second reservoirs 10 and 11, respectively, are spaced laterally from each other along the bypass conduit BC and in series communication with each other. First and second measurements are taken in the reservoirs 10 and 11 as represented by the electrometers 12 and 13, respectively. The flow P is measured by the flow meter 14 (shown schematically).

With reference to FIG. 3, these first and second measurements are arithmetically converted, as follows:

$$Q = \frac{i_1}{P[1 - i_2/i_1]}$$

wherein $Q$ = the charge density of the fluid in the bypass conduit means (Coulombs/cubic meter);

$i_1$ = the electrical current generated by the fluid in the first reservoir means and flowing to ground (amperes);

$i_2$ = the electrical current generated by the fluid in the second reservoir means and flowing to ground (amperes); and $P$ = the flow rate of fluid in the bypass conduit means (cubic meters/second).

Accordingly, the measurement of the charge density of the fluid flowing in the conduit is made independently of residence and relaxation times of the fluid, and therefore alleviates the problem of measurement inaccuracy due to the motion of the fluid.

Figure 4:
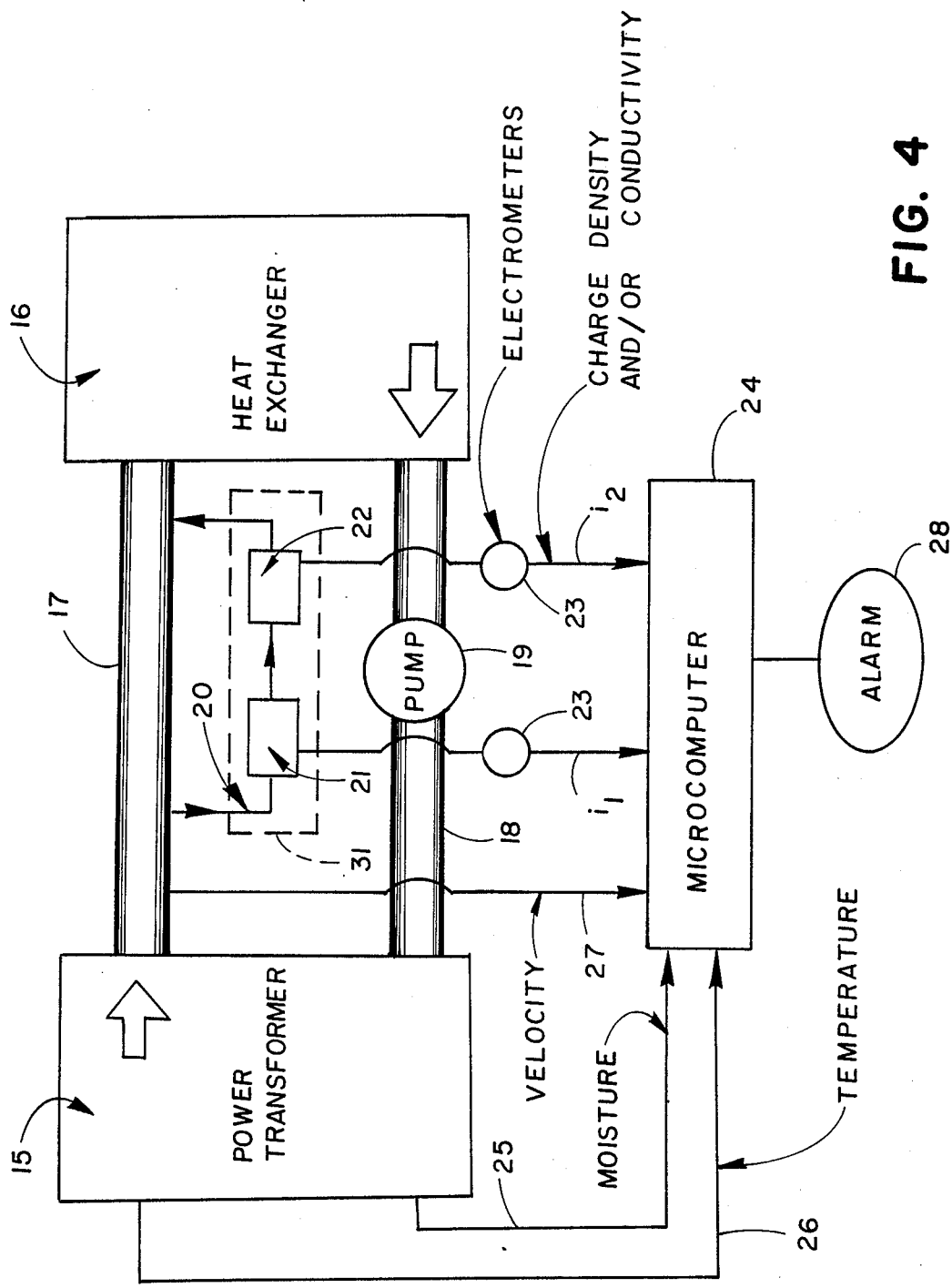
FIG. 4 is a schematic diagram of a preferred embodiment utilizing the teachings of the present invention in a cooling system for a power transformer.

With reference to FIG. 4, there is illustrated a preferred embodiment of the teachings of the present invention. There, a power transformer 15 uses a coolant fluid (such as oil) which is pumped into (and out of) a suitable radiator or heat exchanger 16 by conduits 17 and 18, respectively, and a pump 19. The bypass conduit 20 contains respective tandem fluid chambers or reservoirs 21 and 22, respectively. Measurements of the fluid relaxation currents are taken from the respective reservoirs 21 and 22 (via electrometers 23) and are fed into a microprocessor or microcomputer 24. The charge density generated in the oil/cellulose environment of the power transformer 15 (or other electrical power equipment) depends not only on the velocity but also on temperature, moisture, conductivity, imposed AC stress, etc., thereby making interpretation of a raw charge density measurement difficult. However, the use of the small microcomputer 24 to undertake the measurement and control the transmission of data to a remote location can also be used to condition the measurement through the use of parameter performance envelopes based on the measurement of some of these other key parameters. Thus, for example, additional measurements of moisture and temperature are inputted into the microcomputer 24 via suitable sensors (schematically denoted at 25 and 26, respectively). A further input of fluid velocity (schematically denoted at 27) is inputted into the microcomputer 24.

The microcomputer 24 may trigger an alarm 28 or, if desired, an automatic shutdown mechanism (not shown) whenever the single arithmetically-conditioned measurement of the charge density in the coolant oil in the power transformer 15 exceeds a predetermined threshold value.

Figure 5:
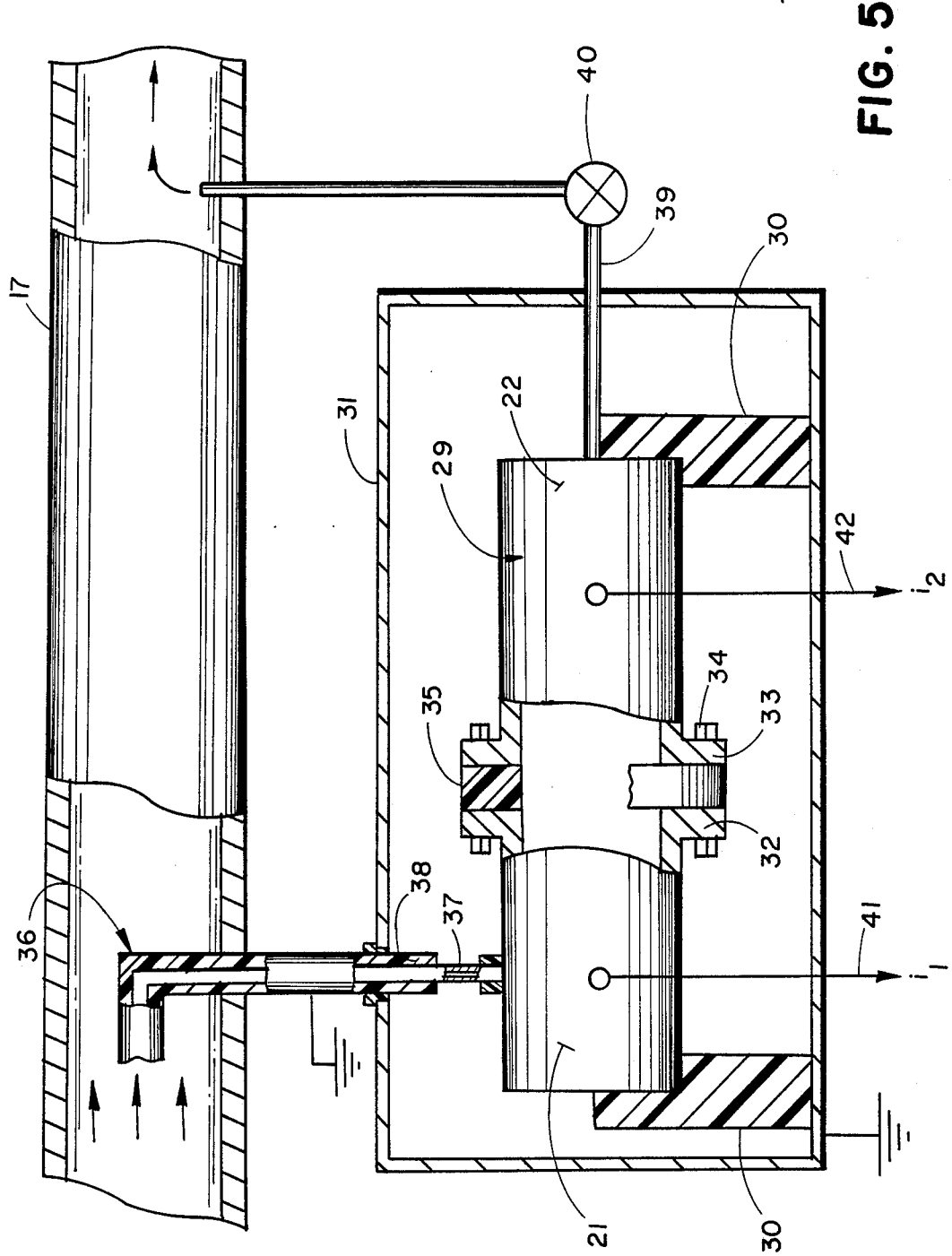
FIG. 5 is an enlarged portion of FIG. 4, showing the details of the bypass conduit means, and further showing the manner in which the measurements are taken in the respective electrically-insulated reservoirs or chambers in the bypass conduit mean.

With reference to FIG. 5, the bypass conduit 20 may constitute a cylindrical tank 29 supported on blocks 30 made of polytetrafluorethylene (or other suitable material) within a suitable metallic housing 31. The housing 31 provides a grounded metallic screen for the tank 29. The tank 29 has a central insulated section, thereby forming the desired respective chambers or reservoirs 21 and 22. This insulated section is formed by respective flanges 32 and 33 (secured together by suitable insulating bolts 34) with an annular insulated member 35 therebetween. A sampling probe 36 leads to the first reservoir 21 in the tank 29, and the sampling probe 36 includes an inner conduit 37 and a grounded shield 38. The second reservoir 22 in the tank 29 is connected to a return pipe 39, and the return pipe 39 is provided with a flow meter 40. The first and second measurements (denoted at 41 and 42, respectively) are taken in the first and second reservoirs 21 and 22, respectively, via suitable coaxial connectors (not shown) and are inputted to the microcomputer 24 (via suitable electrometer elements 23).

In a pipe application, the small bypass flow is driven by the differential pressure created by the design of entry and exit ports. However, the invention can also be used to sample fluid from discrete points in equipment by the use of a small pump (not shown).

In addition to the obvious advantages of the tandem charge monitor of the present invention (that is, independent of relaxation time and residence time, simple calculation of charge density, and a device with no moving parts) the tandem charge monitor can also be used as an on-line conductivity cell with a slight modification. More specifically, one of the electrometers can be substituted by a battery and conduction current between two chambers can be monitored with the existing second electrometer element. Thus the conductivity can be calculated from the calibrated cell constant of the tandem charge monitor, an applied battery voltage, and the measured current.

Figure 6:
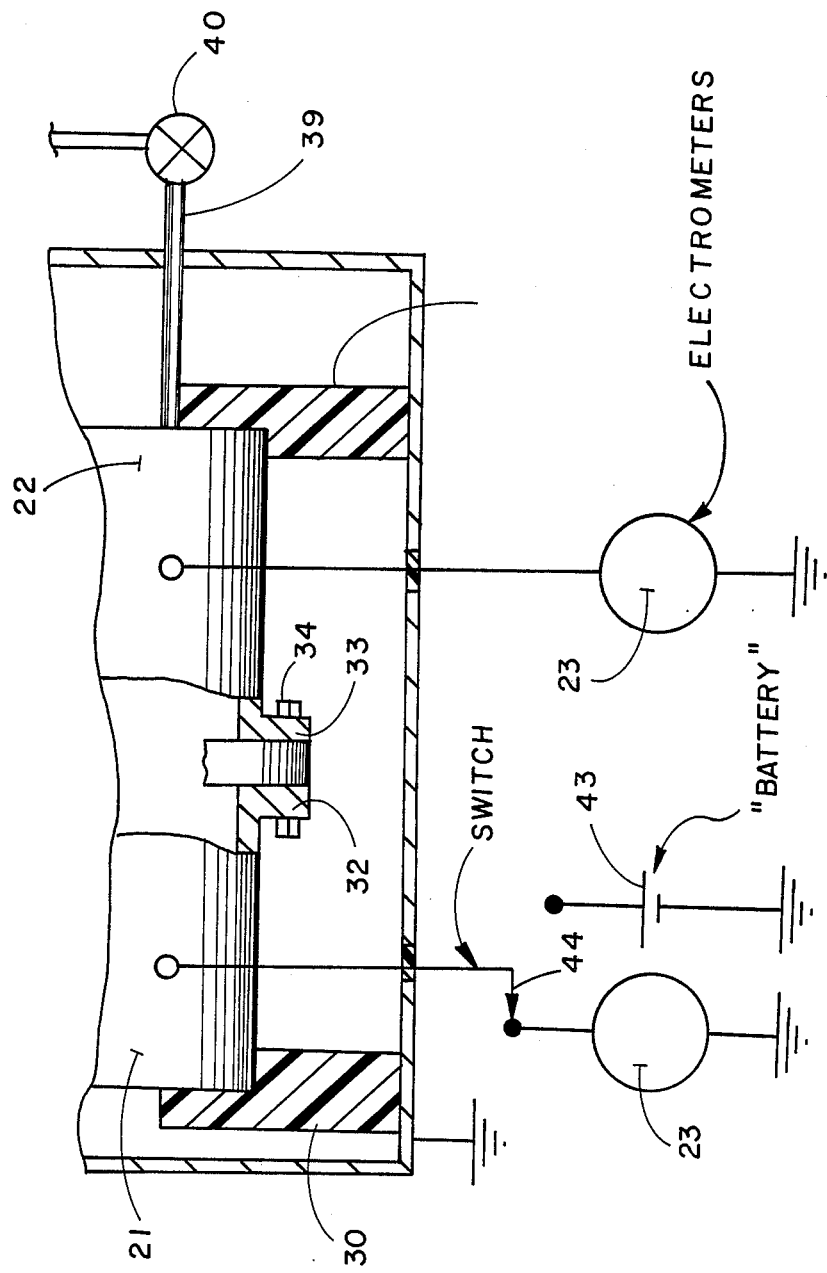
FIG. 6 corresponds to a portion of FIG. 5, but illustrates a schematic representation of another aspect of the present invention, wherein, in an alternate operating mode, the same components of the system may be utilized for measuring the fluid conductivity.

Accordingly, and with reference to FIG. 6, there is illustrated (schematically) how the microcomputer 24 (or other programmed computer means) may also be utilized to measure the fluid conductivity, as well as monitoring the charge density in the fluid. More specifically, the microcomputer 24 may be programmed to introduce a small electrical voltage (represented schematically by the battery 43) into one of the chambers or reservoirs in the bypass conduit (such as in the reservoir 11) and, thereafter, the microcomputer 24 may take a reading of the conductivity of the fluid in the chambers 21 and 22, once cell constant has been established for the tandem chambers 21 and 22, respectively. As will be appreciated by those skilled in the art, the microcomputer 24 automatically re-configures the measuring system using the reed switch 44 but using the same components of the system (that is, the same instrumentation) and takes current readings in the appropriate manner to determine the fluid conductivity. This is a further advantage of the present invention, heretofore not available in the prior art.

Accordingly, it will be appreciated by those skilled in the art that the present invention provides an improved apparatus and method which does not require that the relaxation is complete (that is, it does not matter that some of the charge from the entering fluid is carried out of the downstream chamber) and is independent of the fluid conductivity. Thus, the present invention is suitable for use in large power transformers and provides a simple, robust and reliable means to measure the charge density in the circulating oil due to the streaming electrification process inherent in the pumping of the fluid. Nor is it necessary, using the teachings of the present invention, to have an unduly long bypass conduit; indeed, in applications involving relatively-high flow rates, this source of error inherent in the prior art has now been obviated. The measure of the charge density, using the teachings of the present invention, is independent of both the conductivity of the fluid in the bypass conduit, and of the residence time of the fluid in the electrically-insulated tandem chambers (or reservoirs) in the bypass conduit. Moreover, with the programmed microcomputer, the same components of the system of the present invention may be used (alternately) to measure the conductivity of the fluid. The system has no moving parts, thereby generating good reliability. The measurement section is simple and robust and may be adapted to hostile environments. Additionally, the invention may be used as a self-contained instrument utilizing analog electronics.

Figure 7:
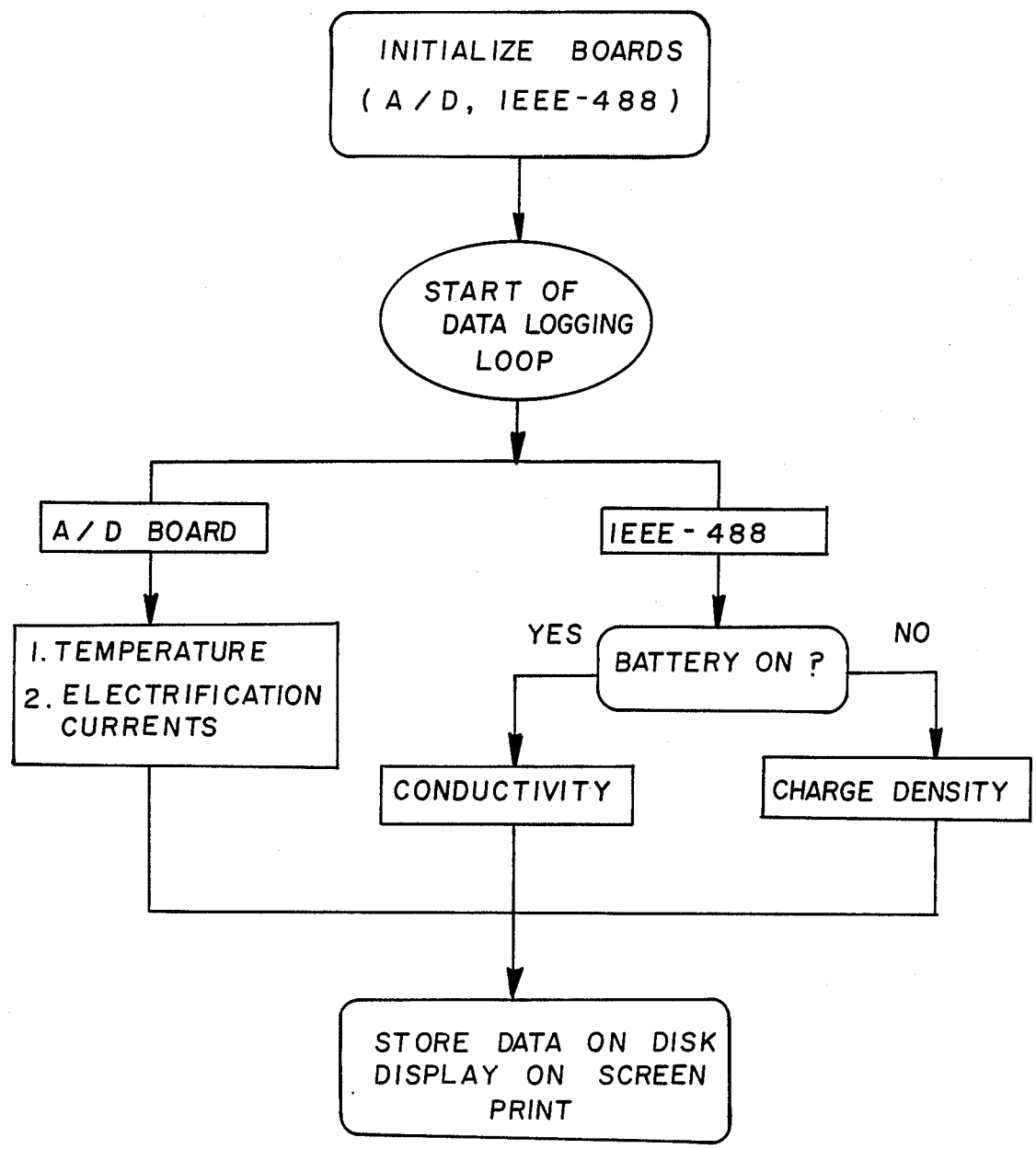
FIG. 7 is a "flow chart" for the programmed operation of the microcomputer means of the present invention.

With reference to FIG. 7, there is illustrated a "flow chart" for the programmed operation of the microcomputer 24.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. In combination with an apparatus for measuring the quantity of static electric charges carried by a fluid flowing through a primary conduit means, wherein a bypass conduit means is provided in a substantially parallel configuration with the primary conduit means for intercepting the flow of fluid therein and is electrically insulated therefrom, wherein a portion of the fluid is temporarily diverted from the primary conduit means into the bypass conduit means, and wherein the charge density of the fluid in the bypass conduit means is continually measured while the fluid is flowing therein at a rate which is less than the rate of the fluid flowing in the primary conduit means; a first reservoir means formed in the bypass conduit means, a second reservoir means formed in the bypass conduit means, laterally spaced from the first reservoir means and in series communication therewith, means for taking a first measurement of the electrical relaxation current associated with the fluid in the first reservoir means and flowing to ground, means for taking a second measurement of the electrical relaxation current associated with the fluid in the second reservoir means and flowing to ground, and means for arithmetic conversion of the first and second measurements into a single measure representative of the charge in the fluid, such that the single measure is independent of both the conductivity of the fluid and of the residence time of the fluid in the first and second reservoirs.

2. The combination of claim 1, wherein the first and second reservoirs are substantially identical.

3. The combination of claim 1, wherein the last-named means for arithmetic conversion of the first and second measurements utilizes the equation:

$$Q = \frac{i_1}{P[1 - i_2/i_1]}$$

wherein

Q = the charge density of the fluid in the bypass conduit means (Coulombs/cubic meter);
$i_1$ = the electrical current generated by the fluid in the first reservoir means and flowing to ground (amperes);
$i_2$ = the electrical current generated by the fluid in the second reservoir means and flowing to ground (amperes); and
P = the flow rate of fluid in the bypass conduit means (cubic meters/second).

4. The combination of claim 1, wherein the means for arithmetic conversion further comprises a microcomputer means.

5. The combination of claim 4, wherein the microcomputer means measures additional fluid properties including temperature moisture and conductivity, and wherein the microcomputer conditions the measurement of fluid charge density through the use of parameter performance envelopes based on the measurements of the additional properties.

6. In a method for measuring the quantity of static electrical charge carried by a fluid flowing through a primary conduit means, wherein a bypass conduit means is provided in a substantially parallel configuration with the primary conduit means for intercepting the flow of fluid therein and is electrically insulated therefrom, wherein a portion of the fluid is temporarily diverted from the primary conduit means into the bypass conduit means, and wherein the charge density of the fluid in the bypass conduit means is continually measured while the fluid is flowing therein at a rate which is less than the rate of the fluid flowing in the primary conduit means; the improvement comprising the steps of providing a first reservoir means in the bypass conduit means, providing a second reservoir means in the bypass conduit means, laterally spaced from the first reservoir means and in series communication therewith, taking a first measurement of the electrical relaxation current associated with the fluid in the first reservoir means and flowing to ground, taking a second measurement of the electrical relaxation current associated with the fluid in the second reservoir means and flowing to ground, and arithmetically converting the first and second measurements into a single measure representative of the charge in the fluid, such that the single measure is independent of both the conductivity of the fluid and of the residence time of the fluid in the first and second reservoirs.

7. The improvement of claim 6, wherein the last-named step of arithmetically converting the first and second measurements utilizes the equation:

$$Q = \frac{i_1}{P[1 - i_2/i_1]}$$

wherein
Q = the charge density of the fluid in the bypass conduit means (Coulombs/cubic meter);
$i_1$ = the electrical current generated by the fluid in the first reservoir means and flowing to ground (amperes);
$i_2$ = the electrical current generated by the fluid in the second reservoir means and flowing to ground (amperes); and
P = the flow rate of fluid in the bypass conduit means (cubic meters/second).

8. The improvement of claim 7, wherein the last-named step of arithmetically converting the first and second measurements further comprises the step of inputting the first and second measurements to a microcomputer for arithmetic conversion therein.

9. The improvement of claim 8, wherein the last-named step of arithmetic conversion by the microcomputer further comprises the step of measuring other system properties including temperature, moisture, conductivity and AC stress, and wherein the microcomputer conditions the measurement of fluid charge density on the basis of measurements of the other system properties through the use of parameter performance envelopes.

10. In a power transformer having a coolant circulated therein, wherein the coolant is pumped out of the transformer and into a heat exchanger through a conduit, the combination of a bypass conduit, means for diverting a portion of the coolant into the bypass conduit, a first reservoir means formed in the bypass conduit, a second reservoir means formed in the bypass conduit means, laterally spaced from the first reservoir means and in series communication therewith, means for continuously taking a first measurement of the electrical relaxation current associated with fluid in the first reservoir means and flowing to ground, means for continuously taking a second measurement of the electrical relaxation current associated with the fluid in the second reservoir means and flowing to ground, and means for arithmetically converting the first and second measurements into a single measure representative of the charge in the fluid, such that the single measure is independent of both the conductivity of the fluid and of the residence time of the fluid in the first and second reservoirs, and wherein the last-named means for arithmetically converting the first and second measurements utilizes the equation:

$$Q = \frac{i_1}{P[1 - i_2/i_1]}$$

wherein
Q = the charge density of the fluid in the bypass conduit means (Coulombs/cubic meter);
$i_1$ = the electrical current generated by the fluid in the first reservoir means and flowing to ground (amperes);
$i_2$ = the electrical current generated by the fluid in the second reservoir means and flowing to ground (amperes); and
P = the flow rate of fluid in the bypass conduit means (cubic meters/second).

11. The improvement of claim 10, wherein the means for arithmetically converting further comprises a microcomputer means.

12. The improvement of claim 11, wherein the microcomputer means measures additional fluid properties including temperature, moisture, conductivity and imposed AC stress, and wherein the microcomputer conditions the measurement of fluid charge density through the use of parameter performance envelopes based on the measurements of additional properties.

13. In a power transformer having a coolant circulated therein, wherein the coolant is pumped out of the transformer and into a heat exchanger through a conduit, the combination of a bypass conduit, means for diverting a portion of the coolant into the bypass conduit, means for taking a first measurement of the electrical relaxation current associated with the fluid in the bypass conduit and flowing to ground, means for taking a second measurement of the electrical relaxation current associated with the fluid in the bypass conduit and flowing to ground at a location in the bypass conduit which is spaced from the location where the first measurement is taken in the bypass conduit, means for arithmetically converting the first and second measurements into a single measure of charge density in the fluid, such that the single measure is independent of both the conductivity of the fluid and of the residence time of the fluid in the first and second reservoirs, wherein the last-named means for arithmetically converting the first and second measurements utilizes the equation:

$$Q = \frac{i_1}{P[1 - i_2/i_1]}$$

wherein
- Q = the charge density of the fluid in the bypass conduit (Coulombs/cubic meter);
- $i_1$ = the first measurement of the electrical current generated by the fluid in the bypass conduit and flowing to ground (amperes);
- $i_2$ = the second measurement of the electrical current generated by the fluid in the bypass conduit and flowing to ground (amperes); and
- P = the flow rate of fluid in the bypass conduit (cubic meters/second);

a microcomputer means for receiving and processing the first and second measurements in the arithmetically converting means, and means responsive to the microprocessor means for taking corrective action when the single measure representative of charge density in the fluid exceeds a predetermined threshold level.

14. The combination of claim 13, wherein the first and second measurements are taken in first and second reservoirs, respectively, formed in the bypass conduit, the first and second reservoirs being laterally spaced from each other and in series communication therewith.

15. The combination of claim 13, wherein the microcomputer has additional inputs of the system properties in the power transformer, including temperature, moisture, conductivity and AC stress, and wherein the microcomputer conditions the measurement of fluid charge density by the measurement of the other system properties through the use of parameter performance envelopes.

16. The combination of claim 13, wherein the first and second measurements are taken continuously.

17. In an electrical apparatus having a coolant circulated by means of a pump and a conduit system, wherein static electrical charges are progressively built up leading to significant charge density in the fluid or on the surfaces thereof, and wherein in the event of a spark, there is a risk of fire, explosion or internal damage due to the electrostatic field associated with the charge density, the improvement in means for measuring the charge density, comprising a bypass conduit for intercepting at least a portion of the coolant in the conduit system, means providing a grounded metallic screen for the bypass conduit, a sampling probe between the conduit system and the bypass conduit, a grounded shield for the sampling probe, the bypass conduit having first and second chambers formed therein and electrically insulated from each other, means for taking a first measurement of the current associated with the coolant in the first chamber and flowing to ground, means for taking a second measurement of the current associated with the coolant in the second chamber and flowing to ground, and means for converting the first and second measurements into a single measure representative of the charge density in the coolant and independent of the conductivity of the coolant.

18. The improvement of claim 17, wherein the bypass conduit comprises a cylindrical tank having a central section provided with respective cooperating flanges, an annular insulated member between the flanges, and means for securing the flanges together, thereby forming the first and second electrically-insulated chambers.

19. The improvement of claim 17, wherein the electrical apparatus comprises a power transformer, and wherein the coolant comprises an oil circulated between the power transformer and the external heat exchanger.

20. The improvement of claim 17, further including a microcomputer for arithmetically converting the first and second measurements.

21. The improvement of claim 20, wherein the microcomputer utilizes the equation:

$$Q = \frac{i_1}{P[1 - i_2/i_1]}$$

wherein
- Q = the charge density of the fluid in the bypass conduit (Coulombs/cubic meter);
- $i_1$ = the first measurement of the electrical current generated by the fluid in the bypass conduit and flowing to ground (amperes);
- $i_2$ = the second measurement of the electrical current generated by the fluid in the bypass conduit and flowing to ground (amperes); and
- P = the flow rate of fluid in the bypass conduit (cubic meters/second);

22. The improvement of claim 20, wherein the microcomputer further has inputs of moisture, temperature, conductivity, imposed AC stress and velocity of the coolant in the conduit system.

23. In combination, a primary conduit having a fluid flowing therein, a bypass conduit for intercepting at least a portion of the fluid flowing in the primary conduit, a grounded shield means for the bypass conduit, the bypass conduit having first and second chambers formed therein, means for electrically insulating the first chamber from the second chamber, means for taking a first measurement of the current associated with the fluid in the first chamber and flowing to ground, means for taking a second measurement of the current associated with the fluid in the second chamber and flowing to ground, means including a programmed computer for converting the first and second measurements into a single measure representative of the charge in the fluid, whereby the single measure is independent of the both the conductivity of the fluid and of the residence time of the fluid in the first and second chambers, and the programmed computer having alternately-selectable means for measuring the conductivity of the fluid in the bypass conduit, such that the combination can measure conductivity of the fluid as well as providing a monitor of the charge density in the fluid.

24. In a system for measuring the charge density of a fluid being pumped through a main conduit, the combination of a parallel bypass conduit for sampling the fluid in the main conduit, monitoring means within the bypass conduit and having respective system components for measuring the charge density in the bulk of the fluid at spaced-apart locations in the bypass conduit, a grounded metallic shield for the respective system components in the bypass conduit, the monitoring means including means for measuring the charge density of the fluid in the main conduit independently of the conductivity of the fluid, and further including alternately-selectable means for measuring the conductivity of the fluid independently of the charge density of the fluid and using the same components of the monitoring means.

25. The system of claim 24, further including means for taking corrective action if the monitored charge density exceeds a predetermined threshold.

* * * * *